United States Patent
Castle et al.

(10) Patent No.: US 10,456,831 B2
(45) Date of Patent: Oct. 29, 2019

(54) DETECTION OF BLOCKAGE IN INTERNAL PASSAGES OF GAS TURBINE ENGINE COMPONENTS

(71) Applicant: UNITED TECHNOLOGIES CORPORATION, Farmington, CT (US)

(72) Inventors: Lea Kennard Castle, Vernon, CT (US); Steven Bruce Gautschi, Milton, MA (US); James Tilsley Auxier, Bloomfield, CT (US)

(73) Assignee: United Technologies Corporation, Farmington, CT (US)

( * ) Notice: Subject to any disclaimer, the term of this patent is extended or adjusted under 35 U.S.C. 154(b) by 54 days.

(21) Appl. No.: 15/421,502

(22) Filed: Feb. 1, 2017

(65) Prior Publication Data

US 2018/0214941 A1    Aug. 2, 2018

(51) Int. Cl.
| | | |
|---|---|---|
| *B22D 29/00* | (2006.01) | |
| *B22D 25/02* | (2006.01) | |
| *B22C 9/24* | (2006.01) | |
| *B22C 9/10* | (2006.01) | |
| *B22C 9/04* | (2006.01) | |
| *G01N 23/04* | (2018.01) | |

(Continued)

(52) U.S. Cl.
CPC .............. *B22D 29/002* (2013.01); *B22C 9/04* (2013.01); *B22C 9/10* (2013.01); *B22C 9/24* (2013.01); *B22D 25/02* (2013.01); *B22D 46/00* (2013.01); *G01N 23/04* (2013.01); *G01N 23/18* (2013.01)

(58) Field of Classification Search
CPC ........ B22D 29/002; B22D 25/02; B22C 9/04; B22C 9/10; B22C 9/24
See application file for complete search history.

(56) References Cited

U.S. PATENT DOCUMENTS

| | | |
|---|---|---|
| 2,475,596 A | 7/1949 | Dawson |
| 2,883,549 A | 4/1959 | Betz |

(Continued)

FOREIGN PATENT DOCUMENTS

EP    0634963    1/1995

OTHER PUBLICATIONS

Extended European Search Report for EP Application No. 18154124.4, dated Jun. 20, 2018.

*Primary Examiner* — Kevin P Kerns
*Assistant Examiner* — Steven S Ha
(74) *Attorney, Agent, or Firm* — Carlson, Gaskey & Olds, P.C.

(57) ABSTRACT

A method of forming a component includes the steps of placing a core into a mold and pouring a component material around the core. The component material is allowed to solidify. The core is then removed from within the material, leaving a component having at least a first and a second cavity formed by the core. A first filler material is moved into the first cavity, and a second filler material is moved into the second cavity. The component is inspected for the presence of an apparent residual core within the first cavity and the second cavity. The location is identified of the apparent residual core from the core based upon an identification of whether the location of the apparent residual core is in the first or second filler materials. A method of inspecting a component formed by investment casting is also disclosed.

18 Claims, 1 Drawing Sheet

(51) Int. Cl.
*B22D 46/00* (2006.01)
*G01N 23/18* (2018.01)

(56) References Cited

U.S. PATENT DOCUMENTS

| | | | |
|---|---|---|---|
| 3,624,397 A | | 11/1971 | Honeycutt et al. |
| 4,983,841 A | | 1/1991 | Stewart et al. |
| 5,242,007 A | | 9/1993 | Remmers et al. |
| 5,465,780 A | * | 11/1995 | Muntner .................. B22C 9/04 |
| | | | 164/369 |
| 2005/0255598 A1 | | 11/2005 | Broutin et al. |

* cited by examiner

DETECTION OF BLOCKAGE IN INTERNAL PASSAGES OF GAS TURBINE ENGINE COMPONENTS

BACKGROUND OF THE INVENTION

This application relates to a method of detecting residual ceramic core in a final gas turbine engine component.

Gas turbine engines are known and typically include a fan delivering air into a bypass duct as propulsion air and into a compressor as core airflow. The air is compressed in the compressor and delivered into a combustor where it is mixed with fuel and ignited. Products of the combustion pass downstream over turbine components driving them to rotate.

As can be appreciated, the turbine components become quite hot when exposed to the products of combustion. As such, it is known to supply cooling air to internal passages in the turbine components.

One way to form internal passages in the turbine engine component is through investment casting. In investment casting, a core is formed in a mold, typically out of a ceramic material. That core is then placed in another mold and wax is molded around the core. The waxed and captured core is then covered with more ceramic material, which builds up an outer layer of ceramic outwardly of the wax, otherwise known as a casting shell.

The wax is then melted away and the remaining casting shell is then placed into an investment casting furnace where a molten metal is poured into a casting shell and resultantly encapsulates the core. This then forms a metal component having complex internal cooling structure. The outer ceramic layer is then removed and the inner ceramic core is leached away. This leaves internal passages.

However, the leaching process is not always as efficient as would be desirable. In particular, in blind internal passages and internal cavities with circuitous paths, it is often the case that residual ceramic core material may remain. It can be difficult to distinguish such residual ceramic material as opposed to the material of the component. Such residual ceramic material can provide a blockage or restriction to airflow through cooling chambers, which is undesirable.

It has been proposed to include a material in the cavities after the leaching that can be viewed utilizing radiation evaluation, such as X-ray to identify residual ceramic.

Recently, the challenges on gas turbine engine components has increased dramatically and the shape and size of the cooling channels has become much more complex.

SUMMARY OF THE INVENTION

In a featured embodiment, a method of forming a component includes the steps of placing a core into a mold and pouring a component material around the core. The component material is allowed to solidify. The core is then removed from within the material, leaving a component having at least a first and a second cavity formed by the core. A first filler material is moved into the first cavity, and a second filler material is moved into the second cavity. The component is inspected for the presence of an apparent residual core within the first cavity and the second cavity. The location is identified of the apparent residual core from the core based upon an identification of whether the location of the apparent residual core is in the first or second filler materials.

In another embodiment according to the previous embodiment, the location of the second cavity at least partially overlaps the location of the first cavity when viewed from a side of the component.

In another embodiment according to any of the previous embodiments, the inspecting step creates an image of the first and second cavity with the second cavity superimposed over the first cavity.

In another embodiment according to any of the previous embodiments, the first filler material has a different atomic weight than the second filler material. The different atomic weights are both greater than an atomic weight of the component material.

In another embodiment according to any of the previous embodiments, the first cavity is a central cavity and the second cavity extends between the central cavity and an outer surface of the component.

In another embodiment according to any of the previous embodiments, the component includes an airfoil and the central cavity extends along a radial length of the component and wherein there are a plurality of the second cavities on both of two sides of the central cavity.

In another embodiment according to any of the previous embodiments, if a residual core material is identified, then a leaching process is repeated.

In another embodiment according to any of the previous embodiments, if apparent residual core material is identified, then a step is taken prior to the repeated leaching process to ensure the first and second filler materials completely fill the first and second cavities to ensure that the apparent residual core is not a void in the filler materials.

In another embodiment according to any of the previous embodiments, the inspection is through x-ray radiation.

In another embodiment according to any of the previous embodiments, the component is a gas turbine engine component, and the first and second cavities are first and second passages.

In another embodiment according to any of the previous embodiments, the first passage is a central cavity and the second passage extends between the central cavity and an outer surface of the component.

In another embodiment according to any of the previous embodiments, the component includes an airfoil and the central cavity extends along a radial length of the component and wherein there are a plurality of the second passages on both of two sides of the central cavity.

In another embodiment according to any of the previous embodiments, if a residual core is identified, then a leaching process is repeated.

In another embodiment according to any of the previous embodiments, if apparent residual core material is identified, then a step is taken prior to the repeated leaching process to ensure the first and second filler materials completely fill the first and second passages to ensure that the apparent residual core is not a void in the filler materials.

In another embodiment according to any of the previous embodiments, the inspection is through radiation.

In another embodiment according to any of the previous embodiments, if a residual core material is identified, then a leaching process is repeated.

In another embodiment according to any of the previous embodiments, if an apparent residual core material is identified, then a step is taken prior to the repeated leaching process to ensure the first and second filler materials completely fill the first and second passages to ensure that the apparent residual core is not a void in the filler materials.

In another embodiment according to any of the previous embodiments, the inspection is through radiation.

In another embodiment according to any of the previous embodiments, the inspection is through x-ray radiation.

In another embodiment according to any of the previous embodiments, the first filler material has a different atomic weight than the second filler material. The different atomic weights are both greater than an atomic weight of the component material.

In another featured embodiment, a method of inspecting an article formed by investment casting using a ceramic inner core includes the steps of receiving the article with the ceramic inner core removed. The article has a first and a second passage formed by the ceramic inner core. A first filler material is moved into the first passage, and a second filler material is moved into the second passage. The article is inspected for the presence of an apparent residual core within the first passage and the second passage. The location is identified of the apparent residual core from the core based upon an identification of whether the location of the apparent residual core is in the first or second filler materials.

These and other features may be best understood from the following drawings and specification.

DETAILED DESCRIPTION

Figure 1:
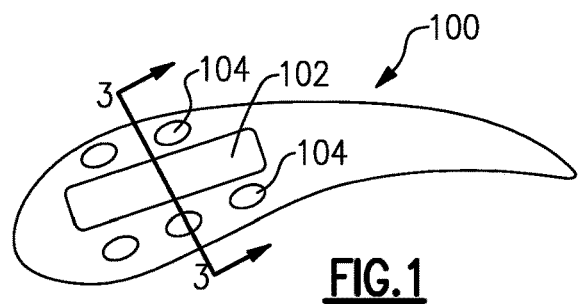
FIG. 1 schematically shows a gas turbine engine component.

A gas turbine engine component 100, shown as an airfoil such as a turbine blade, is illustrated in FIG. 1. A central cooling chamber 102 is formed, and outer end cooling cavities 104 are formed on both sides of the channel 102. While particular channels and chambers are shown, any number of other passages may be formed.

Figure 2A:
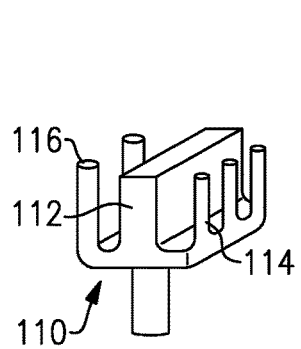
FIG. 2A shows a first core.

FIG. 2A shows a ceramic core 110 which may be utilized to form the passages 102/104. As shown, a central portion 112 will form the passage 102, while side portions 114 and 116 will form the passages 104.

Figure 2B:
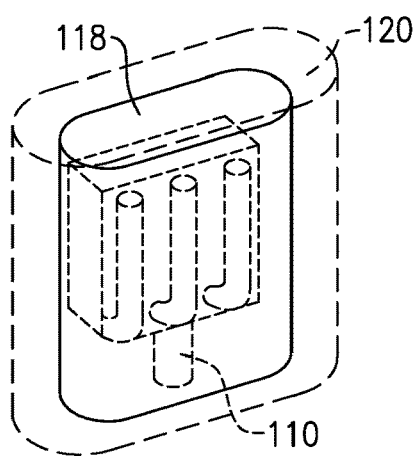
FIG. 2B shows an intermediate step.

FIG. 2B shows an intermediate step. The core 110 is embedded within wax 118, and additional ceramic material 120 is formed around the wax 118. The wax 118 is then melted away, leaving the ceramic 110 and 120.

Metal is poured into the cavity left by the wax. After the metal is solidified, the ceramic on the outside 120 is broken away and the interior ceramic core 110 is leached away. This should leave a final gas turbine engine component having internal passages as shown in FIG. 1.

Figure 3A:
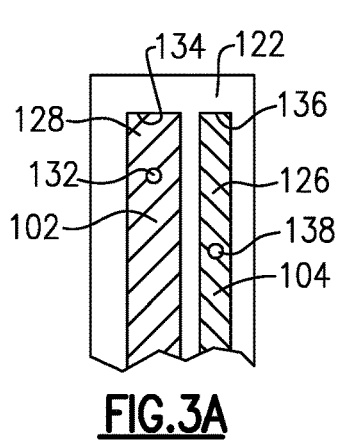
FIG. 3A shows a formed component in an inspection step.

As shown in FIG. 3A, the passage 102 has a dead end 134. Outer cavity 104 also has a dead end 136.

The process performed for leaching may have difficulty completely cleaning out such dead end passages or cavities as there is no "flow through." As such, residual ceramic core is shown at 132 and 138. To identify these residuals, a first material 128 is inserted into the passage 102, and a second material 126 is inserted into the passage(s) 104. The two materials are distinct, and preferably have distinct atomic weight. As an example, one of the materials may be a Ta/W/Re based atomic weight materials while the others could be Zr/Nb/Mu/Ru based atomic weight materials. The master alloy of the component may be a nickel-based atomic weight material.

Figure 3B:
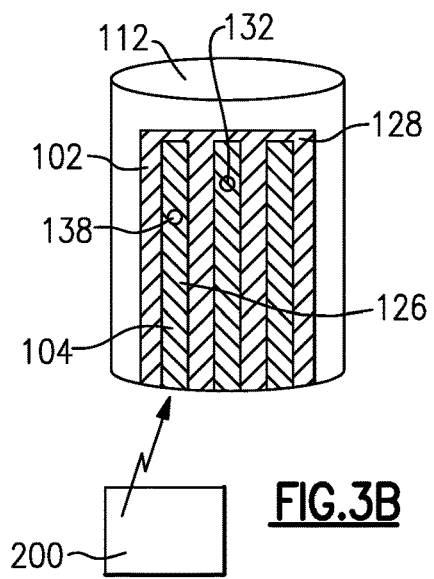
FIG. 3B shows a result of the FIG. 3A inspection step.

An x-ray process is shown schematically at 200 in FIG. 3B. The passages 104 overlap locations of the central passage 102. This is illustrated in FIG. 3B.

Since there are different atomic weight to the filler materials, there would be different gray scales of the resultant x-ray image. The atomic weight of the filler materials is preferably higher than the atomic weight of the material forming the component. The residual ceramic will be virtually invisible to the x-rays passing through the component material. Typically, gas turbine engine components formed by such a method may be nickel-based super alloy castings, and ceramics have lower atomic weight than such materials.

FIG. 3B shows an image of residual ceramic 138 which does not have an overlap of the material found in the passages 104, and thus would be a residual ceramic core which is likely in the passage 104.

On the other hand, the image shows an apparent residual ceramic core portion 132 which has the second material 126 found in the passage 104 apparently overlaid over its image. This would be indicative of the location of the material 132 being in the passage 102.

A worker of ordinary skill in the art would thus know where to expect these residual ceramic materials to be found.

As a first step should an apparent residual ceramic material be identified, the component should be re-evaluated by taking steps to ensure the first and second filler materials completely fill the first and second passages. This could ensure apparent residual material is not simply a void in the filler materials. However, once it is determined that residual core material is likely present, then a subsequent leaching process may be provided.

A method of forming a component with this disclosure could be said to include the steps of placing a core into a mold and pouring a component material around the core, and allowing the component material to solidify. Then the core is removed from within the material, leaving a component having at least a first and a second cavity formed by the core. A first filler material is moved into the first cavity, and a second filler material is moved into the second cavity. The component is inspected for the presence of an apparent residual core within the first cavity and the second cavity, and the location of the apparent residual core is identified based upon an identification of whether the location of the apparent residual core is in the first or second filler materials.

Stated another way, a method of inspecting an article formed by investment casting using a ceramic inner core includes the steps of receiving the article with the ceramic inner core removed. The article has a first and a second passage formed by the ceramic inner core. A first filler material is moved into the first passage, and a second filler material is moved into the second passage. The article is inspected for the presence of an apparent residual core within the first passage and the second passage. The location of the apparent residual core is identified based upon an identification of whether the location of the apparent residual core is in the first or second filler materials.

While the art of investment casting is explained somewhat schematically here, it is complex. Workers of ordinary skill in this art would understand that there are a number of options and details in addition to those briefly disclosed here to form the components.

In addition, while one particular component and geometry is illustrated, many other variations would benefit from this disclosure. As an example, some components may be formed with several cores. The cores may form passages which do not communicate with each other. Again, a worker of ordinary skill in the art would recognize many of these potential variations.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A method of forming a component comprising:
placing a core into a mold and pouring a component material around the core;
allowing the component material to solidify, and then removing the core from within said material, leaving a component having at least a first and a second cavity formed by said core;
moving a first filler material into the first cavity, and moving a second filler material into the second cavity;
inspecting said component for a presence of an apparent residual core within said first cavity and said second cavity, and identifying a location of the apparent residual core from said core based upon an identification of whether the location of the apparent residual core is in the first or second filler materials, and said first filler material has a different atomic weight than said second filler material, and wherein said atomic weights of said first and second filler materials are both different than an atomic weight of the component material;
wherein the location of said second cavity at least partially overlaps the location of said first cavity when viewed from a side of said component; and
wherein said different atomic weights of said first and second filler material are both greater than an atomic weight of the component material.

2. The method as set forth in claim 1, wherein said first cavity is a central cavity and said second cavity extends between said central cavity and an outer surface of the component.

3. The method as set forth in claim 2, wherein said component includes an airfoil and said central cavity extends along a radial length of said component and wherein there are a plurality of said second cavities on two sides of said central cavity.

4. The method as set forth in claim 1, wherein if a residual core material is identified, then a leaching process is repeated.

5. The method as set forth in claim 4, wherein if apparent residual core material is identified, then a step is taken prior to the repeated leaching process to ensure the first and second filler materials completely fill the first and second cavities to ensure that the apparent residual core is not a void in the filler materials.

6. The method as set forth in claim 5, wherein the inspection is through radiation.

7. The method as set forth in claim 1, wherein said component is a gas turbine engine component, and said first and second cavities are first and second passages.

8. The method as set forth in claim 7, wherein said first passage is a central cavity and said second passage extends between said central cavity and an outer surface of the component.

9. The method as set forth in claim 8, wherein said component includes an airfoil and said central cavity extends along a radial length of said component and wherein there are a plurality of said second passages on two sides of said central cavity.

10. The method as set forth in claim 9, wherein if a residual core is identified, then a leaching process is repeated.

11. The method as set forth in claim 10, wherein if apparent residual core material is identified, then a step is taken prior to the repeated leaching process to ensure the first and second filler materials completely fill the first and second passages to ensure that the apparent residual core is not a void in the filler materials.

12. The method as set forth in claim 11, wherein the inspection is through radiation.

13. The method as set forth in claim 1, wherein if a residual core material is identified, then a leaching process is repeated.

14. The method as set forth in claim 13, wherein if an apparent residual core material is identified, then a step is taken prior to the repeated leaching process to ensure the first and second filler materials completely fill the first and second passages to ensure that the apparent residual core is not a void in the filler materials.

15. The method as set forth in claim 1, wherein the inspection is through radiation.

16. The method as set forth in claim 15, wherein the inspection is through x-ray radiation.

17. A method of forming a component comprising:
placing a core into a mold and pouring a component material around the core;
allowing the component material to solidify, and then removing the core from within said material, leaving a component having at least a first and a second cavity formed by said core;
moving a first filler material into the first cavity, and moving a second filler material into the second cavity;
inspecting said component for a presence of an apparent residual core within said first cavity and said second cavity, and identifying a location of the apparent residual core from said core based upon an identification of whether the location of the apparent residual core is in the first or second filler materials, and said first filler material has a different atomic weight that said second filler material, and wherein said atomic weights of said first and second filler materials are both different than an atomic weight of the component material;
wherein said different atomic weights of said first and second filler material are both greater than an atomic weight of the component material; and
wherein if a residual core material is identified, then a leaching process is repeated.

18. A method of inspecting an article formed by investment casting using a ceramic inner core, comprising the steps of:
receiving the article with the ceramic inner core removed, the article having a first and a second passage formed by the ceramic inner core;
moving a first filler material into the first passage, and moving a second filler material into the second passage; and
inspecting the article for a presence of an apparent residual core within said first passage and said second passage, and identifying a location of the apparent residual core from said core based upon an identification of whether the location of the apparent residual core is in the first or second filler materials; and wherein said first filler material has a different atomic weight than said second filler material, and wherein said different atomic weights are both greater than an atomic weight of the component material.

* * * * *